(12) United States Patent
Prewitt

(10) Patent No.: US 10,092,381 B2
(45) Date of Patent: Oct. 9, 2018

(54) ORTHODONTIC RETAINER CLEANING CASE

(71) Applicant: Mary Julia Prewitt, Wrightsville Beach, NC (US)

(72) Inventor: Mary Julia Prewitt, Wrightsville Beach, NC (US)

(73) Assignee: Mary Julia Prewitt, Sarasota, FL (US)

( * ) Notice: Subject to any disclaimer, the term of this patent is extended or adjusted under 35 U.S.C. 154(b) by 135 days.

(21) Appl. No.: 15/170,596

(22) Filed: Jun. 1, 2016

(65) Prior Publication Data
US 2016/0271656 A1  Sep. 22, 2016

Related U.S. Application Data

(63) Continuation-in-part of application No. 13/006,770, filed on Jan. 14, 2011, now Pat. No. 9,358,084.

(51) Int. Cl.
| | | |
|---|---|---|
| *A61C 17/00* | (2006.01) | |
| *A61C 7/08* | (2006.01) | |
| *A61C 19/00* | (2006.01) | |
| *A45D 44/20* | (2006.01) | |
| *A61L 2/00* | (2006.01) | |

(52) U.S. Cl.
CPC .......... *A61C 17/036* (2013.01); *A45D 44/20* (2013.01); *A61C 7/08* (2013.01); *A61C 19/002* (2013.01); *A61L 2/0088* (2013.01)

(58) Field of Classification Search
CPC .......... B08B 3/08; B08B 11/02; B08B 3/044; B08B 3/10; B08B 3/12; A61C 17/036; A61C 19/002; A61C 7/008; A61C 19/008; A45D 44/20; A47L 25/00; A61L 2/0088; A61L 2/18; A61L 2202/17; B65D 47/32

USPC ..... 206/368.5, 63.5; 128/859; 134/137, 155; D3/294, 203.1, 301; D24/227; D28/73
See application file for complete search history.

(56) References Cited

U.S. PATENT DOCUMENTS

| | | | | |
|---|---|---|---|---|
| 1,683,458 A | * | 9/1928 | Garrison | A61C 17/02 15/21.1 |
| 2,135,503 A | * | 11/1938 | Guntrip | B65D 25/10 206/205 |
| 2,648,344 A | * | 8/1953 | Randolph | G04D 3/083 134/157 |
| 4,966,319 A | * | 1/1990 | Fleming | A45C 11/00 224/615 |
| 5,832,940 A | * | 11/1998 | Embry | A46B 11/0027 132/308 |

(Continued)

FOREIGN PATENT DOCUMENTS

DE       3511305 A1 * 10/1986  ............. A45D 44/20

OTHER PUBLICATIONS

Amazon.com—Cordless Sonic Cleaner—Denture Baths (dated Nov. 2, 2014) (archived at https://web.archive.org/web/20141102062732/http://www.amazon.com:80/Essix-Cordless-Sonic-Cleaner/dp/B0018FNUXU) ("Essix"). (Year: 2014).*

*Primary Examiner* — Joseph L. Perrin
*Assistant Examiner* — Kevin G Lee
(74) *Attorney, Agent, or Firm* — NEO IP

(57) ABSTRACT

A lidded plastic container has a plunger in the lid which pushes dental appliances down into a cleaning solution. The container includes vent holes in its lid to allow gas-evolving cleaning agents to vent without building up pressure inside the container and to drain the fluid from the container.

20 Claims, 15 Drawing Sheets

(56) References Cited

U.S. PATENT DOCUMENTS

| | | | |
|---|---|---|---|
| 2002/0078981 A1* | 6/2002 | Berghash | A61C 17/036 134/135 |
| 2005/0194022 A1* | 9/2005 | Schwartz | B08B 3/12 134/1 |
| 2007/0228079 A1* | 10/2007 | Vogel | B65D 47/0838 222/151 |
| 2010/0043838 A1* | 2/2010 | Foget | A61L 2/18 134/30 |
| 2014/0374282 A1* | 12/2014 | Cinader, Jr. | A61C 19/02 206/63.5 |

* cited by examiner

ORTHODONTIC RETAINER CLEANING CASE

CROSS REFERENCES TO RELATED APPLICATIONS

This application is a continuation-in-part of application Ser. No. 13/006,770, filed Jan. 14, 2011, which is incorporated herein by reference in its entirety.

BACKGROUND OF THE INVENTION

1. Field of the Invention

The present invention relates to an orthodontic retainer cleaning case and, more particularly, to an orthodontic retainer cleaning case having a plunger to submerge retainers in the solution.

2. Description of the Prior Art

Conventional retainer cleaning tablet instructions inform the user to place the retainer in a glass of water, similar to denture cleaning instructions. However, dentures sink in water but clear plastic retainers and clear aligners, such as INVISALIGN® trays, float, resulting in difficulties in surrounding the retainer/aligner with water/cleaning solution. Plastic retainers/aligners also cover the entire enamel surface of the tooth, making removal of bacteria and plaque even more important. Moreover, the clear plastic retainers/aligners are susceptible to scratching, which damages their aesthetics.

Numerous prior art inventions teach cleaning of dental and orthodontic devices:

US Patent Application Publication 2010/0330535 by Prasad Adusimilli et al, published Dec. 30, 2010, teaches a device for cleaning and polishing dentures during denture fabrication.

US Patent Application Publication 2010 007/014225 by Sandra Arce et al, published Jun. 21, 2007, teaches a storage container suitable for cleansing dentures.

U.S. Pat. No. 3,149,358 by G. A Chadbounrne, issued Sep. 22, 1964, teaches a denture plate cleansing cup.

U.S. Pat. No. 5,314,543 by W. E. Elkins et al, issued May 24, 1994, teaches a microwave oven for cleaning a prosthesis.

U.S. Pat. No. 6,390,104 by Steven P. Gagnon, issued May 21, 2002, teaches a denture wash with nozzles and a pump.

U.S. Pat. No. 1,683,458 by H. G. Hall, issued Sep. 4, 1928, teaches a cleaning device with false teeth which is lined with bristles and a cover with a rotatable brush.

European Patent Application EP1110447 by Cheng-Ho Huang, published Jun. 27, 2001, teaches an artificial tooth storage box with multiple compartments.

German Patent Publication DE3511305 by Leopold Immler, published Oct. 2, 1986, teaches a container for dentures, braces and the like.

US Patent Application Publication 2008/0283422 by John M. Jansheski, published Nov. 20, 2008, teaches a dental case for storing a dental guard.

U.S. Pat. No. 7,041,261 by Brian E. Margolis, issued May 9, 2006, teaches a sanitizing sponge container.

U.S. Pat. No. 7,798,159 by Valerie Palfy et al., issued Sep. 21, 2010, teaches an at-home integrated cleaning and disinfection system and method for dental hardware.

U.S. Pat. No. 3,904,058 by Abraham J. Rosenstein, issued Sep. 9, 1975, teaches a combined pocket flask and denture case.

U.S. Pat. No. 6,213,777 by Jeana L. Seitzinger, issued Apr. 10, 2001, teaches an apparatus for cleaning and storing dental appliances and similar articles.

European Patent Application Publication EP0766969 by Domingo Villar Otero, published Apr. 9, 1997, teaches a pacifier boiling device for use in a microwave oven.

U.S. Pat. No. 2,163,862 by Jack Wing, issued Jun. 27, 1939, teaches a holder for dentures and other articles.

SUMMARY OF THE INVENTION

In one aspect of the present invention, a cleaning container for holding a substrate under the surface of a liquid, comprises of a base adapted to hold the liquid; a lid adapted to close against the base; a plunger attached to the lid, the plunger adapted to hold the substrate below the surface of the liquid when the substrate and the liquid are present in the base.

In another aspect of the present invention, a cleaning container comprises a base adapted to hold a cleaning solution; a lid adapted to fit on the base; at least four slots cut through the lid; a disc-shaped plunger descending from an underside of the lid, wherein the plunger is disposed below a surface of the cleaning solution when the cleaning solution is in the cleaning container, wherein the plunger is adapted to hold a bouyant retainer below the surface of the cleaning solution when the retainer and the cleaning solution are present in the base.

These and other features, aspects and advantages of the present invention will become better understood with reference to the following drawings, description and claims.

DETAILED DESCRIPTION OF THE INVENTION

Figure 1:
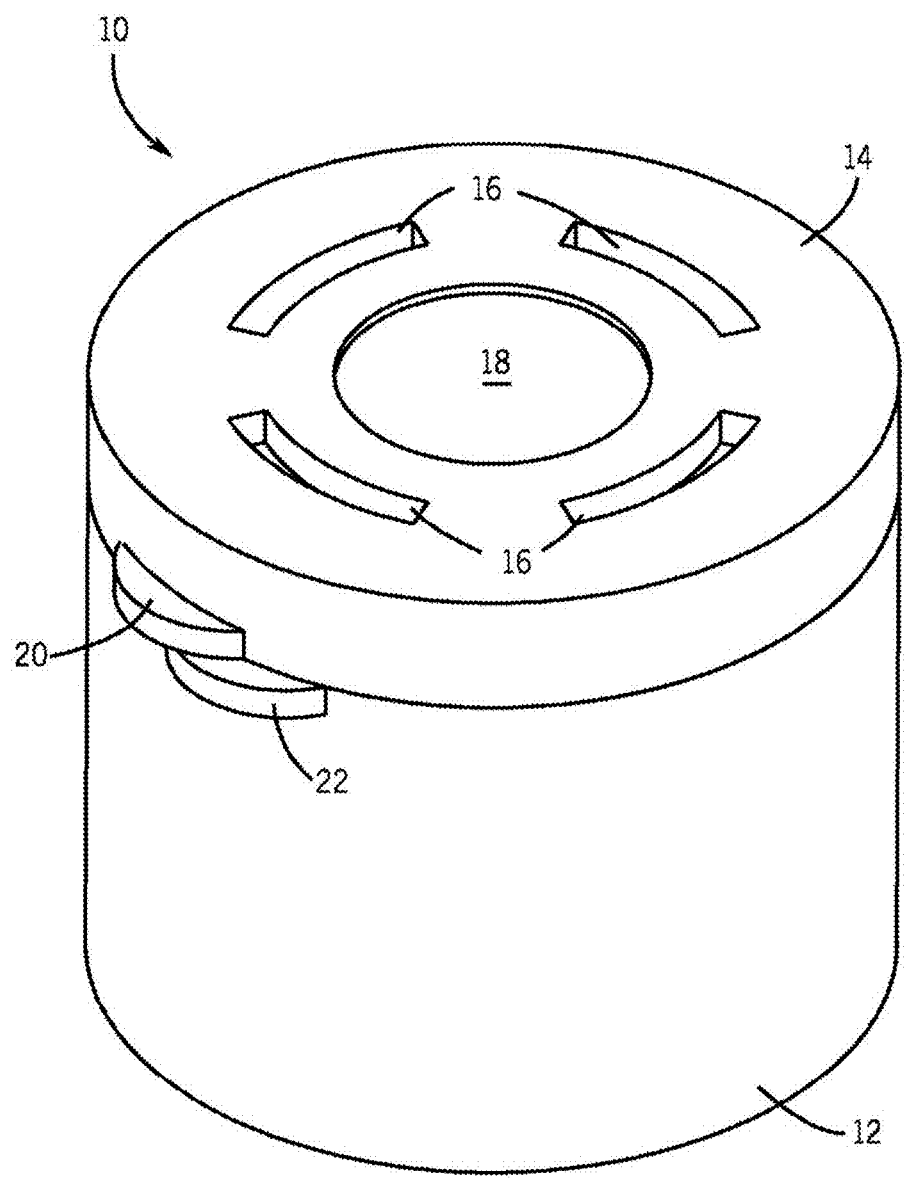
FIG. 1 is a perspective view of a cleaning case according to an exemplary embodiment of the present invention.
Figure 2:
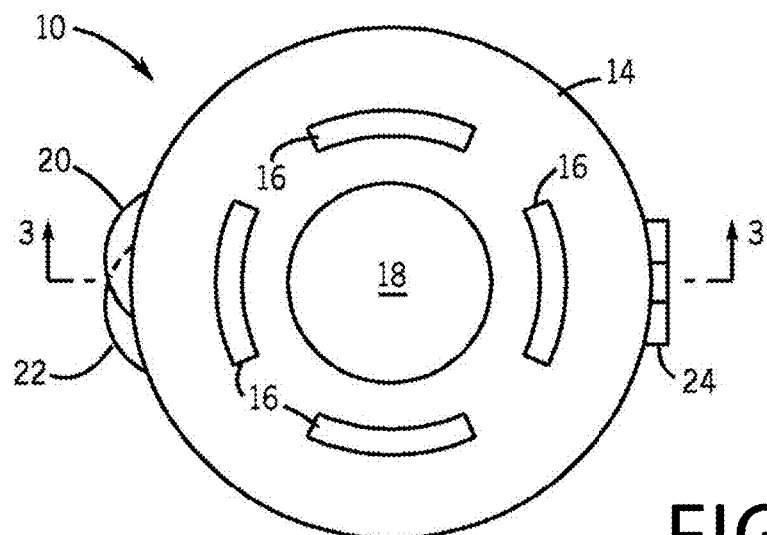
FIG. 2 is a top view of the cleaning case of FIG. 1.
Figure 3:
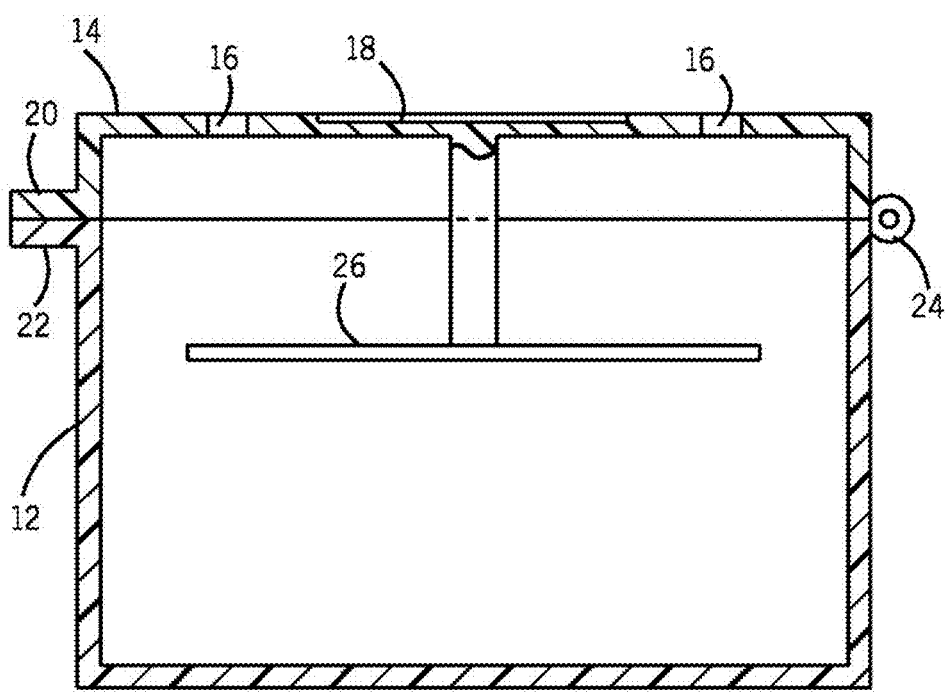
FIG. 3 is a cross-sectional view of the cleaning case of FIG. 1 taken along line 3-3 of FIG. 2.
Figure 4:
FIG. 4 shows a transparent front perspective view of another exemplary embodiment of the present invention.
Figure 5:
FIG. 5 shows a transparent top view of the cleaning case of FIG. 4.
Figure 6:
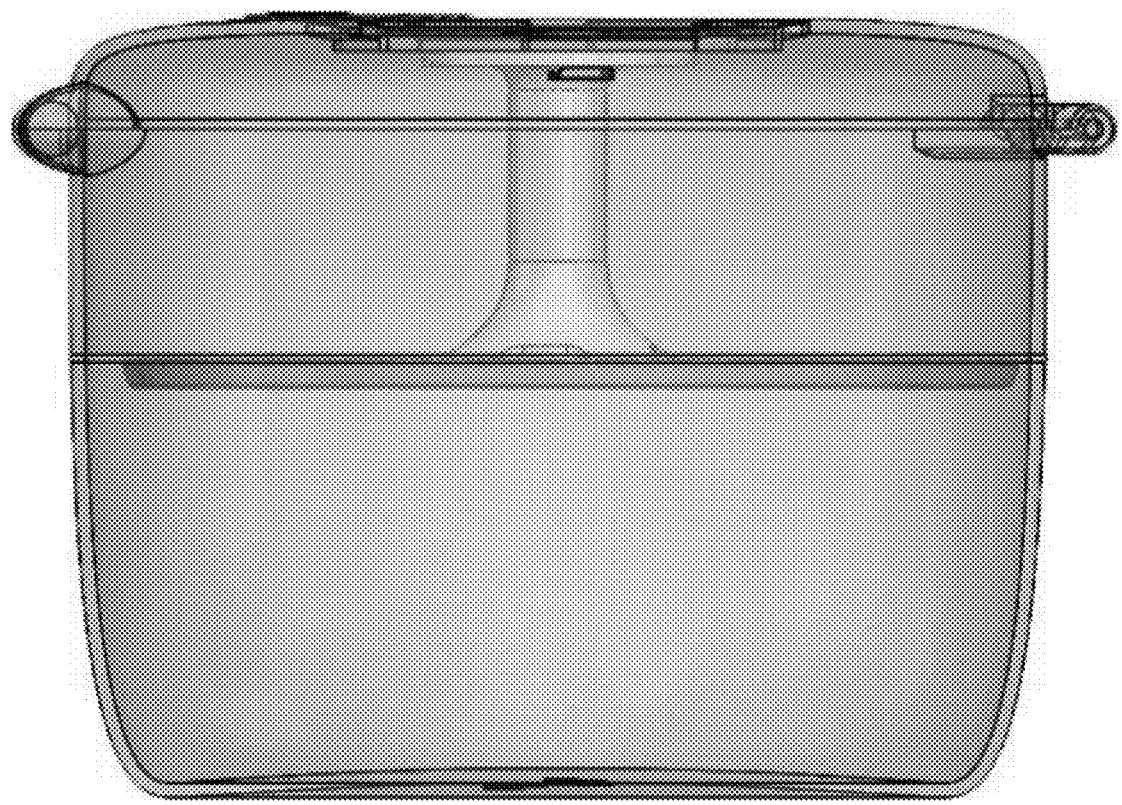
FIG. 6 shows a transparent side view of the cleaning case of FIG. 4.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

None of the prior art provides for the cleaning of clear plastic dental/orthodontic devices, such that the device remains completely submerged and is handled in a way to prevent scratching. Furthermore, none of these provide for a container in which the device can be easily rinsed without the user touching the device or without the risk of damage to the device.

Thus, there is a need for an apparatus for cleaning orthodontic appliances that prevents orthodontic retainers/INVISALIGN trays from floating to the surface of a liquid in their cleaning case and prevents scratching during cleaning.

Broadly, an embodiment of the present invention provides a lidded plastic container that has a plunger in the lid which pushes clear trays (that usually float) down into a cleaning solution. The container includes vent holes in its lid to allow gas evolving cleaning agents to vent without building up pressure inside the container and also to allow draining off the cleaning fluid by inverting the container.

Referring to FIGS. 1 through 16, a cleaning container 10 includes a base 12 and a lid 14. The lid 14 is hingeably attached to the base 12 with a hinge 24. The hinge 24 is of any conventional design, such as a hole and pin design or a living hinge type of design. In an alternative embodiment, the hinge is integral with the lid and base.

The cleaning container is sized to accommodate dental and orthodontic devices, such as retainers, retainer trays, especially vacuum-formed retainers, clear aligners such as INVISALIGN trays, dentures and other dental prosthetics. INVISALIGN trays are described in U.S. Pat. Nos. 6,217,325 and 6,722,880, which are incorporated by reference in their entirety. Herein, when a retainer and/or retainer tray is specified, it is intended that term encompasses the other orthodontic and dental devices previously cited.

The cleaning container 10 is, for example, about 3-5 inches in diameter, typically about 4 inches in diameter, and about 2-4 inches in height, typically about 3 inches in height. In some embodiments, the lid 14 is about ½ inch in height, while the base 12 is about 2.75 inches high. For larger orthodontic or dental devices, the diameter is between about 3 inches and about 6 inches and the height is between about 2 and about 6 inches.

The lid 14 includes one or more vent holes 16. In one embodiment, the vent holes 16 are disposed as slits in the top surface of the lid 14. In another embodiment, the vent is a plurality of curved slots arranged in a circle, operable to allow a closure to fit into them and rotate. The vent holes 16 permit gas from cleaning products to vent without pressure building up in the cleaning container 10. No mechanical parts project through the vent holes of the lid; however, in an embodiment the lid includes a vent-closure mechanism (vent closure) for closing the vents to prevent spillage. The vent holes also function as drain holes for draining the cleaning solution when the container is inverted. These drain holes allow the user to easily drain the fluid without having to dump the contents of the container, including the retainer, into a sink. To save time, a multiplicity of drain holes are provided, such that the fluid drains quickly. Preferably, two to four drain holes are provided.

Once the cleaning fluid has drained, the container can be opened while inverted. In this manner, the retainer/tray never strikes the container sides or bottom, or the plunger disc. This prevents the retainer/tray from rattling around in the container when the container does not include a liquid, preventing damage to the retainer/tray caused by contact with the container sides or bottom. Additionally, the aligner/retainer is able to be rinsed off under a faucet while still on the disc before being removed. Thus, the user never need touch the cleaning solution.

A recess 18 is provided in the lid 14. The recess 18 is used to apply a logo, insignia or the like. The recess 18 is disposed in a central region on the top surface of the lid 14 and the vent or vents are disposed peripherally to the recess. The recess prevents the insignia or logo from being wet by the cleaning fluid when the container is being drained while inverted, thereby preventing the insignia from bleaching and fading over time.

Figure 7:
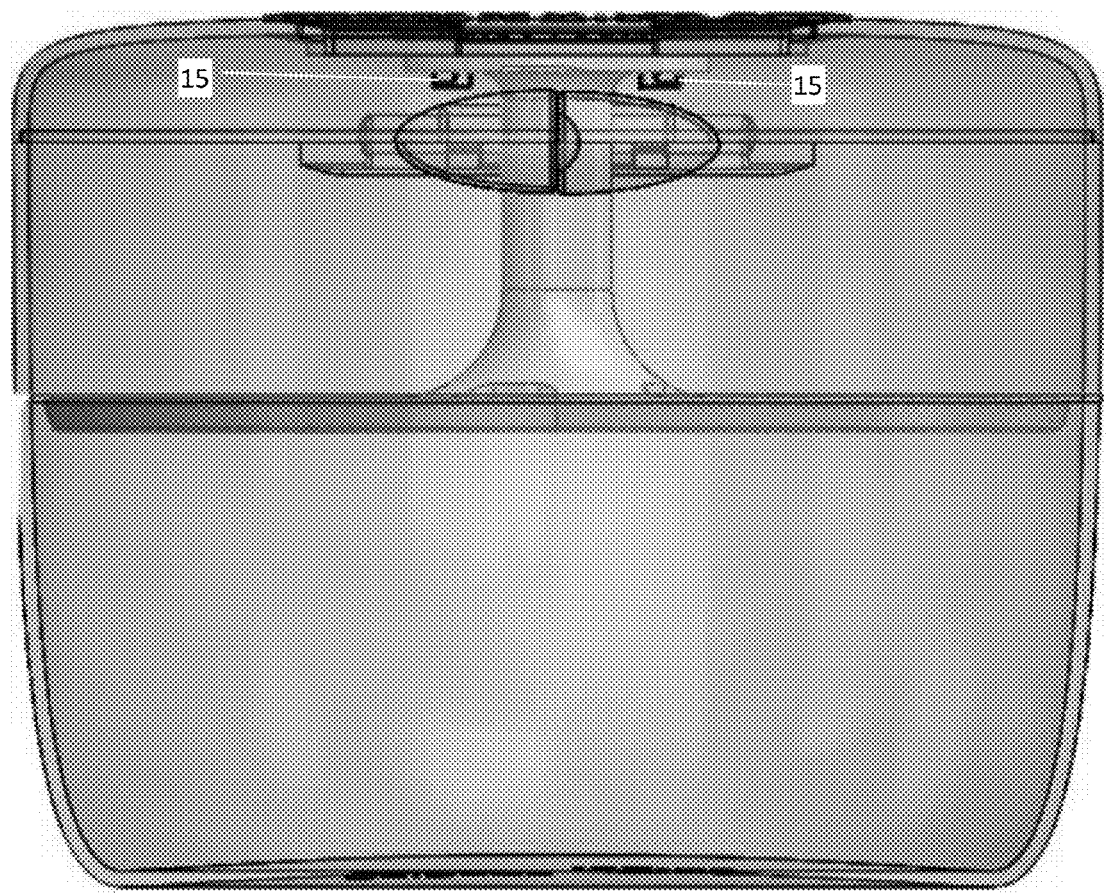
FIG. 7 shows a transparent front view of the cleaning case of FIG. 4.
Figure 8:
FIG. 8 shows a transparent top perspective view of the cleaning case of FIG. 4.

A plunger 26 extends from an underside of the lid 14. The plunger is attached to the underside of the lid and includes a protrusion stem and a disc. The plunger can be attached through various means. For example, the stem can be attached to the lid with a bayonet-type mount 15 (FIG. 7). The plunger 26 is from about 2 to about 4 inches in diameter, typically about 3 inches in diameter. In some embodiments, the plunger 26 is from 0.5 to 1.5 inches smaller in diameter than the diameter of the base 12. The plunger 26 is disposed from about 1 to about 2 inches below the lid, typically about 1.25 inches below the lid to allow the plunger 26 to hold a substrate to be cleaned (such as a retainer tray, a retainer, especially vacuum-formed retainers such as an INVISALIGN tray, or the like, to be held below the surface of cleaning solution disposed in the base 12 of the cleaning container 10. The disc 26 is a flat piece of material, such as plastic, or is slotted, contoured, or the like, to permit the plunger to hold a retainer under cleaning solution disposed in the container 10. Notably, the container contains no protruding parts within the retainer space, herein defined as the space delimited by the container bottom, side walls, and disc, in which the retainer/aligner is positioned.

The lid 14 seals against the base 12 when the lid 14 is closed against the base 12. In some embodiments, the lid 14 includes a protrusion and the base 12 includes an inset adapted to receive the protrusion when the lid 14 is closed on the base 12. The protrusion and inset are, for example, about 2 mm thick and frictionally fit together, for example as a snap-fit closure, to form a seal. In other embodiments, a sealing member (not shown), such as an o-ring, is disposed between the lid 14 and the base 12. In still other embodiments, the lid 14 sits flat against the base 12.

The lid 14 and the base 12 include one or more tabs 20, 22 to aid in opening and closing the container 10. The tabs 20, 22 are offset to provide a leverage point for opening the lid 14 from the base 12. In some embodiments, the tabs 20, 22 include a mechanism to help keep the container 10 closed. For example, the one tab includes a protrusion, while the other includes a socket, where the protrusion fits into the socket when the container 10 is closed. Other configurations of the tabs 20, 22 are within the scope of the present invention. The tabs are sized and shaped to facilitate opening the container while it is inverted, such that the retainer can be retrieved resting on the disc. In this manner, the retainer/tray never strikes the container sides or bottom, or the plunger disc, when draining and removing the retainer/tray from the container. Furthermore, the disc is concave downward so as to prevent the retainer from slipping off the disc when the inverted container is opened. In alternative embodiments, the container 10 includes elements, such as an external brush holder (not shown) for holding a retainer cleaning brush. This holder is useful to keep the retainer cleaning brush close at hand for use before and/or after soaking the retainer in cleaning solution disposed in the container 10.

A user places their retainer in the base 12 of the container 10 and fills the base 12 with about 2 inches of cleaning liquid, or in any case enough liquid to reach at or above the disc when the container is closed, such that the aligner/retainer is submerged. Also, a cleaning tablet is added to the liquid when necessary. The lid 14 is then closed, causing the plunger 26 to push the retainer into the liquid. Once the cleaner has been given the desired working time, the lid 14 is opened and the retainer floats to the surface of the liquid. The retainer can then be removed and the liquid poured out. The container 10 is cleaned and the lid 14 closed on the base 12 for storage.

Alternatively, once the cleaning is finished, the container is inverted and the cleaning fluid drains through the lid vents. Once the fluid has finished draining, the container is opened in the inverted position and the retainer, which is resting on the disc, is removed, or alternatively, is rinsed off under a faucet while still on the disc and then removed.

Thus, the present invention provides a cleaning container for cleaning a retainer, retainer tray and/or an aligner, such as an INVISALIGN tray, which floats in a liquid under the surface of the liquid, in which the device is protected from scratches and in which the user need not touch the device until it is rinsed.

The cleaning container includes a base with at least a bottom adapted to hold the liquid, a lid, and a plunger.

The lid is adapted to close against the base. The lid has a top with at least four vent holes, and a hinge connecting it and the base for hinged opening and closing of the lid.

The plunger is attached to the underside of the lid and includes a protrusion stem and a disc. The protrusion stem is located approximately in the center of the underside of the lid. The disc is flat and slotted to facilitate downward and upward movement of the disc through the liquid. The protrusion stem is immovably affixed perpendicularly to the lid at one end and immovably affixed perpendicularly to the disc at the other end. The disc is adapted to directly hold the retainer or the retainer tray below the surface of the liquid by physically contacting the retainer or the retainer tray from above, wherein the retainer or the retainer tray is not supported by any part of the container from underneath when the retainer or the retainer tray and the liquid are present in the base. Submersion of the retainer without affixing the retainer to the container prevents the possibility of damage to the retainer. Because the aligner, retainer or retainer tray is floating and not held, it is less likely to be scratched if the container is shaken or otherwise jarred. Furthermore, the container contains no protruding parts within the retainer space, which is the space delimited by the container bottom, side walls, and disc. In this manner, the aligner/retainer is less likely to be scratched.

The lid includes a protrusion and the base includes an inset operable to receive the protrusion when the lid is closed against the base.

The base further includes an o-ring that provides a seal between the base and the lid when the lid is closed against the base.

The lid includes a recess in the central region on the top surface of the lid.

The cleaning container includes at least one lid tab disposed on the lid and at least one base tab disposed on the base.

When the lid is closed against the base, the disc is positioned approximately one-third of the distance from the top of the lid to the bottom of the base to submerge the retainer or the retainer tray under the surface of the liquid and allow the hinge to close when the lid is closed against the base. The disc does not contact the container during the closure of the lid, thereby preventing stress on the hinges and the possibility of the disc binding with the container walls.

The at least four vent holes allow gases produced from the interaction of the liquid and the retainer or the retainer tray to vent without building up pressure inside the container. The protrusion, the inset, and the o-ring ensure the lid remains closed against the base during cleaning of the retainer or the retainer tray and the protrusion is inserted in the inset and to ensure that the gases produced from the interaction of the liquid and the retainer or the retainer tray vent through the at least four vent holes instead of through another part of the container.

There is no integrated brush in the container, including no integrated brush on the disc because a brush would likely scratch the clear plastic retainer/aligner. Furthermore, a brush would trap debris, which over time would lead to bacterial contamination of the container or, in any case, general fouling of the retainer or tray. The cleaning container also does not include a motor because any mechanical process risks scratching the retainer/aligner. The disc also does not include spacers or other holders for holding the retainer/aligner or the retainer tray in place in order to prevent the possibility of scratching the retainer or tray against the spacer or other holder if the container is shaken or otherwise jarred, or if the retainer/aligner is accidentally released from the holder.

In a preferred embodiment, the cleaning container, including the base, the lid, the hinge, and the plunger, is formed of a unitary plastic material.

FIGS. 9-16 show alternative embodiments of cleaning cases according to the present invention.

Figure 9:
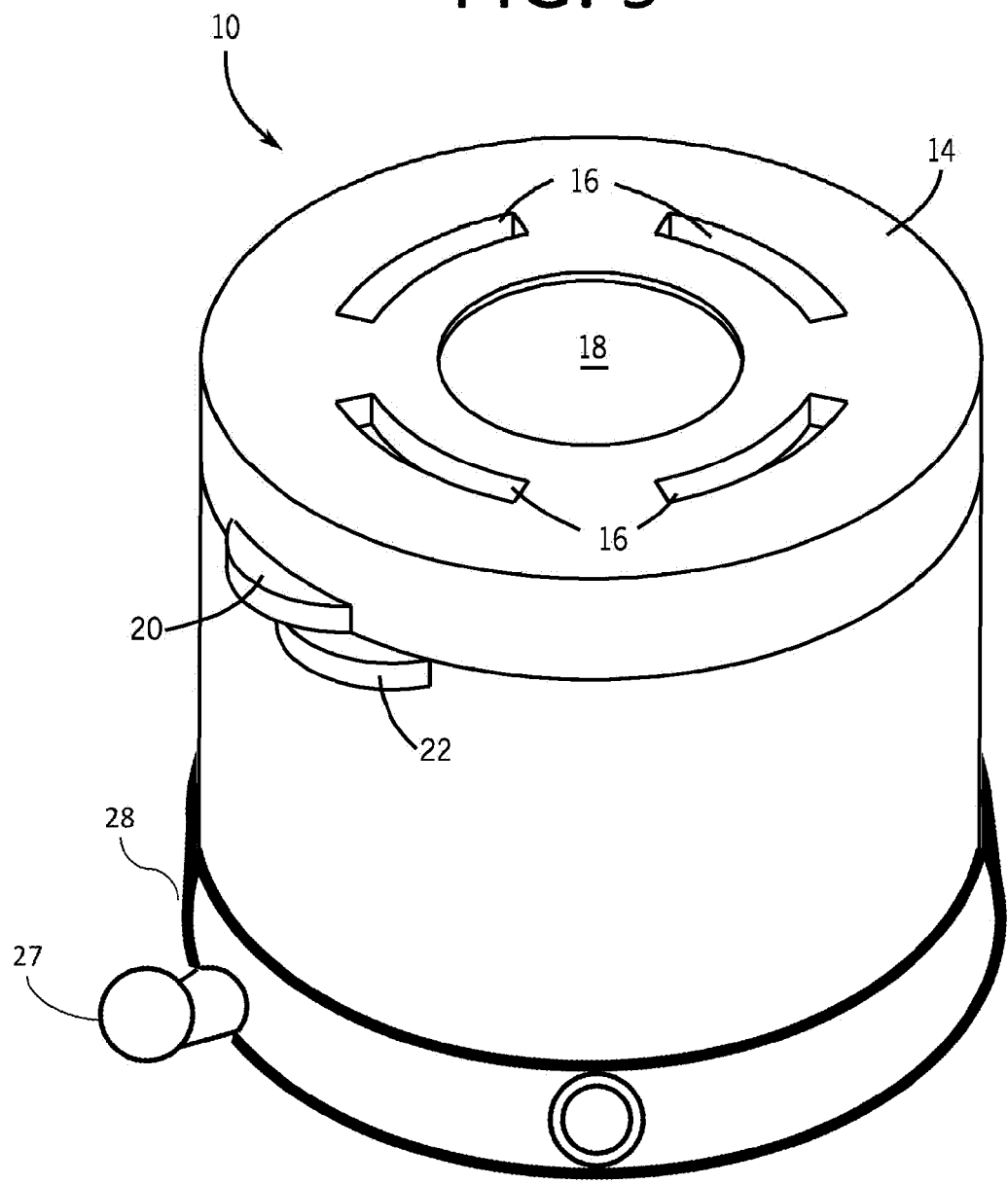
FIG. 9 is a top ¾ perspective view of a cleaning case according to the present invention with an ultrasonic base or sonicator.

FIG. 9 is a top ¾ perspective view of a cleaning case with an ultrasonic base 28. The cleaning case preferable snap-fits into the base. The case can be released from the base by force alone, or through a release mechanism such as a tab or button 25.

Figure 10:
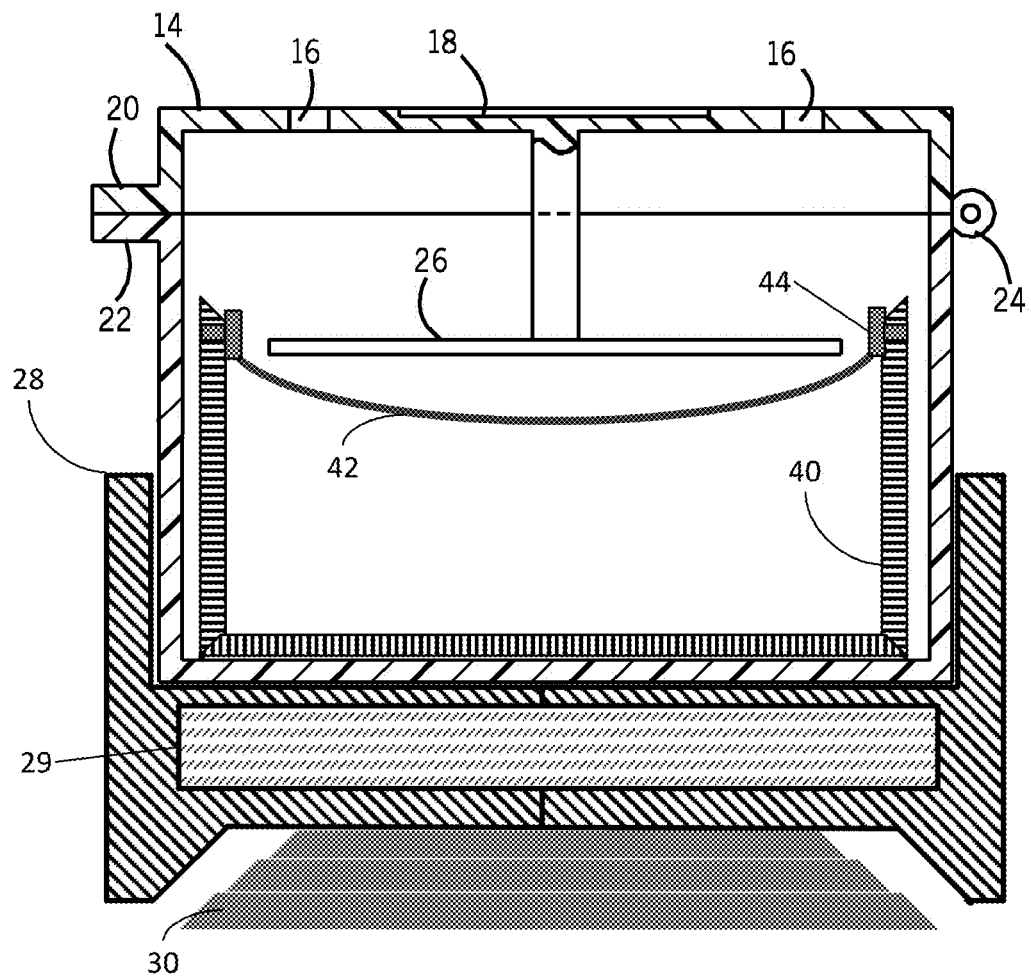
FIG. 10 is a cut-away side view of an example embodiment of the present invention with a suction-adherent ultrasonic base or sonicator and interior strainer basket.

FIG. 10 is a cut-away side view of an example embodiment of the present invention with a suction cup 30 for adherence of an ultrasonic base 28 and an interior strainer basket 40. the suction cup includes a tab (shown as 27 in FIG. 9). The ultrasonic base includes an ultrasonic generator 29. The ultrasonic base is operable to aid in the cleaning of the retainer or retainer tray by emitting ultrasonic waves that vibrate through the container, the liquid, and the retainer or the retainer tray. Advantageously, the ultrasonic base or sonicator loosens and/or removes dirt, buildup, and other impurities from the retainer or retainer tray. The strainer basket 40 includes a handle 42 with hinges 44. The hinges allow the handle to drop below the plunger when the handle is released by the user.

Figure 11:
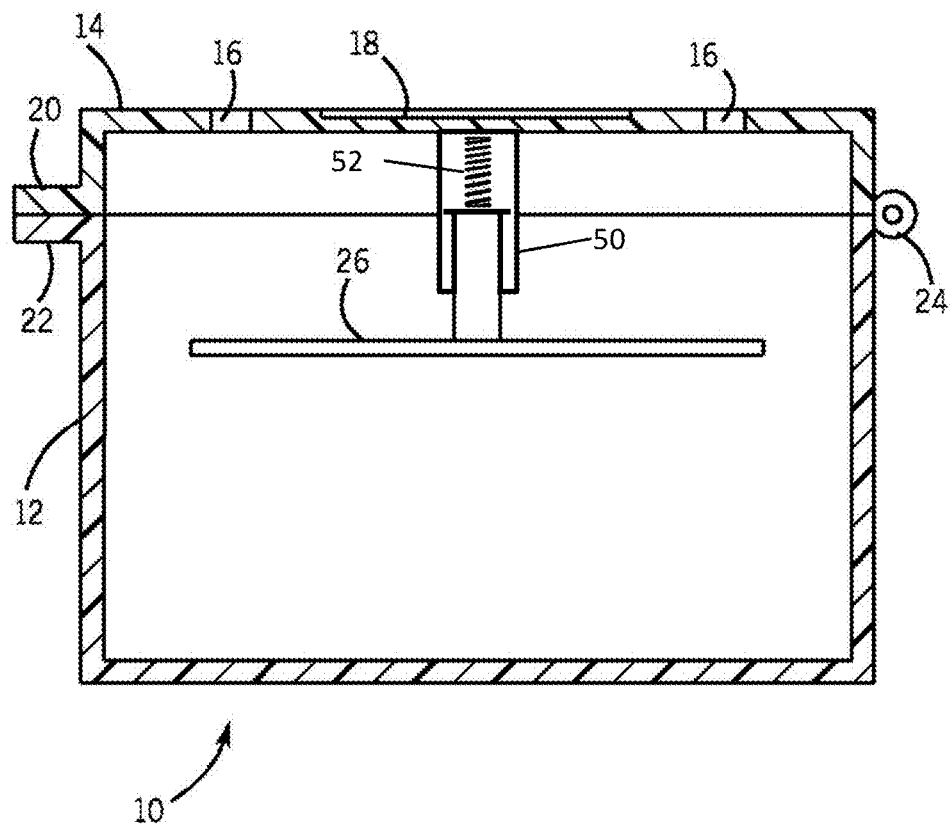
FIG. 11 is a cutaway view side view of the present invention with a spring-loaded telescoping stem.

FIG. 11 is a cutaway side view of the present invention with a spring-loaded telescoping stem 50. The stem includes a spring 52 that forces the plunger down, but allows it to telescope and rise, thus accommodating larger retainers, dentures and other orthodontic devices.

Figure 12:
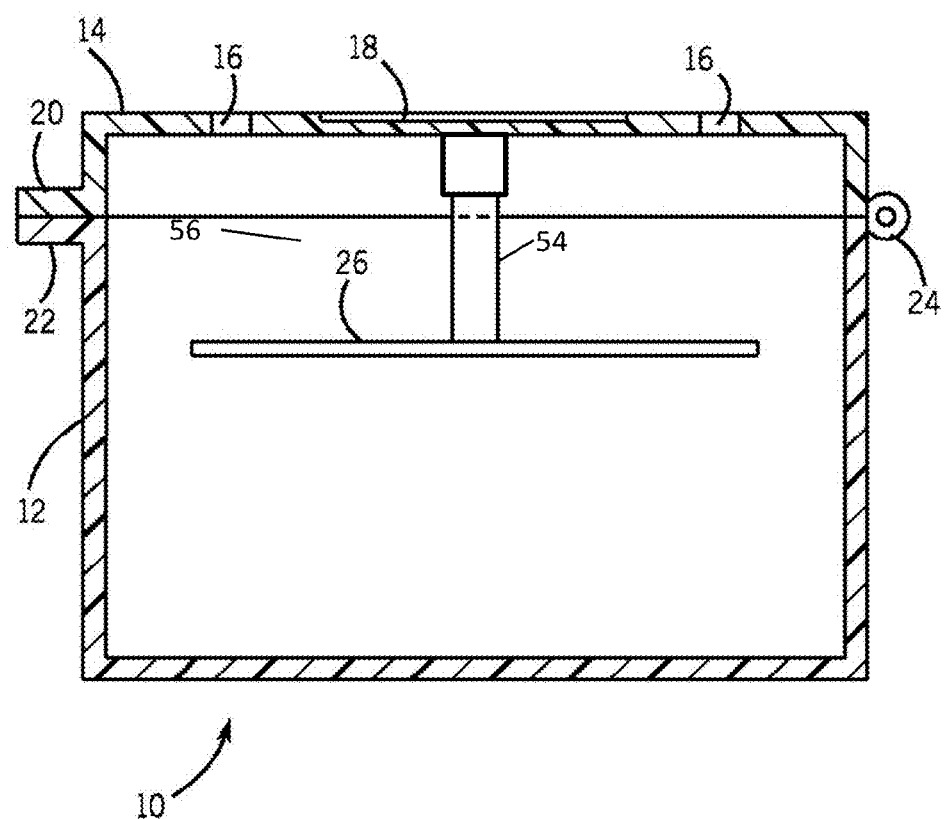
FIG. 12 is a cutaway side view of the present invention with a removable stem and plunger.

FIG. 12 is a cutaway side view of the present invention with a removable stem and plunger 54. The lid includes a stem base connector 56, to which the removable stem and plunger 54 is attached. Any type of connection can be used. For example a snap-fit connection or a screw-type connection can be used.

Figure 13A:
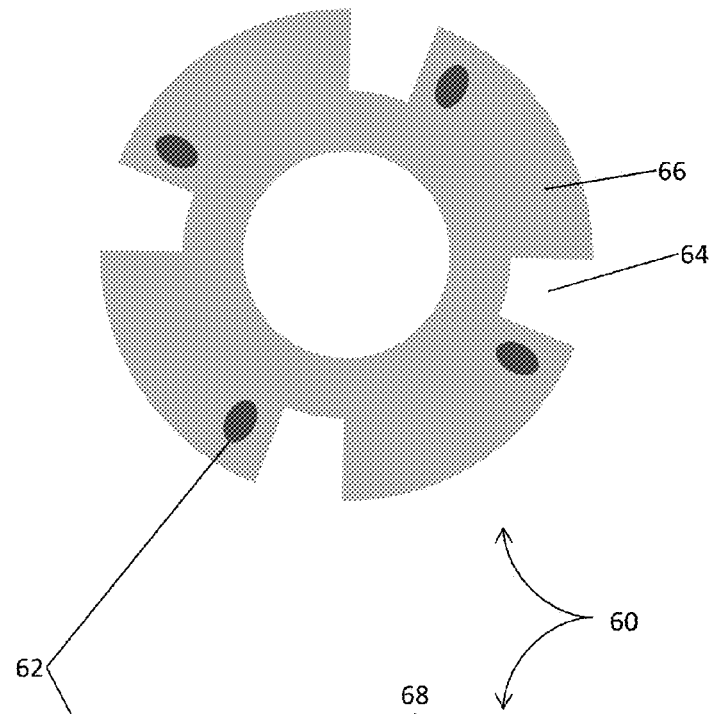
FIG. 13A is a top view of a vent closure for use with a cleaning case with a removable plunger.

FIGS. 13A and B are top views of vent closures. FIG. 13A is a top view of a vent closure, generally described as 60, for use with a cleaning case with a removable plunger. The vent closure 60 includes handles 62 that snap-fit into the lid vents. The handles thus hold the vent closure in the lid and also provide an external handle for rotating the vent closure to different positions (open/closed). The vent closure includes notches 64. These create the openings for the open position. The closure flaps 66 close the vent when the vent closure is rotated into the closed position.

Figure 13B:
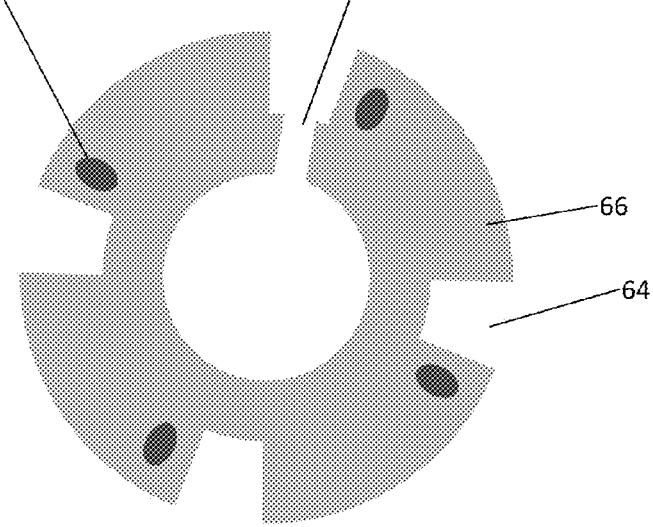
FIG. 13B is a top view of a vent closure for use with a cleaning case with a fixed plunger.

FIG. 13B is a top view of a vent closure 60 for use with a cleaning case with a fixed plunger. This vent closure includes a slot 68 that allows the vent closure to be slipped around the stem.

Figure 14A:
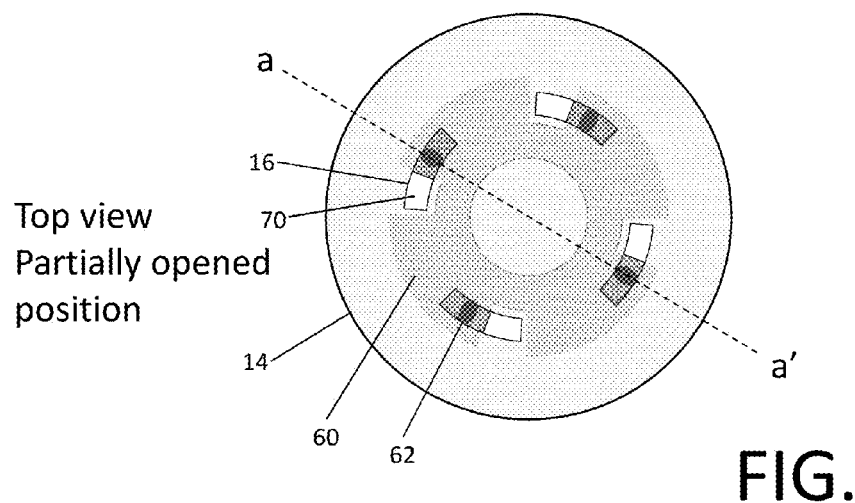
FIG. 14A is a transparent top view of a lid with an installed vent closure in a partially opened position.

FIG. 14A is a transparent top view of a lid 14 with an installed vent closure 60 in a partially opened position. In this diagram, the vents 16 are partially opened. The partial openings are indicated as 70. The lid 14 is concentric with the vent closure 60.

Figure 14B:
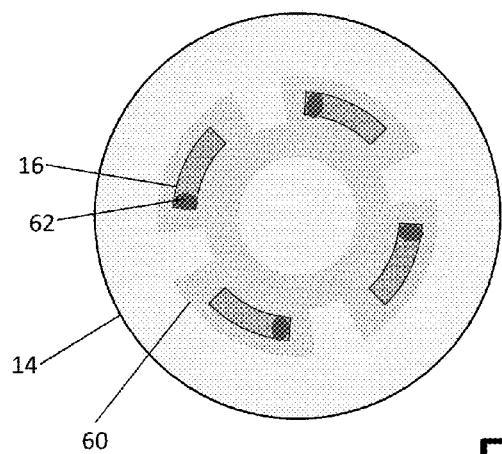
FIG. 14B is a transparent top view of a lid with an installed vent closure in a closed position.

FIG. 14B is a transparent top view of a lid 14 with an installed vent closure 60 in a closed position.

Figure 15A:
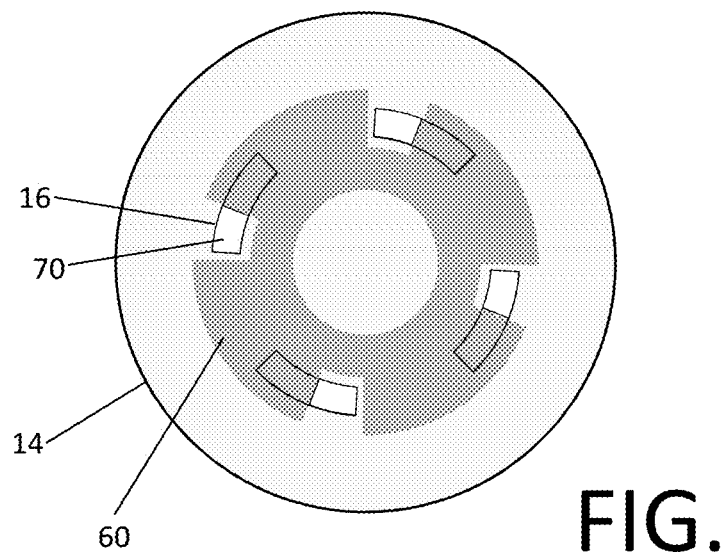
FIG. 15A is a transparent bottom view of a lid with an installed vent closure in a partially opened position.

FIG. 15A is a transparent bottom view of a lid 14 with an installed vent closure 60 in a partially opened position. The vent 16 has a partial vent opening 70. Although the view is transparent, the handles are not shown for clarity.

Figure 15B:
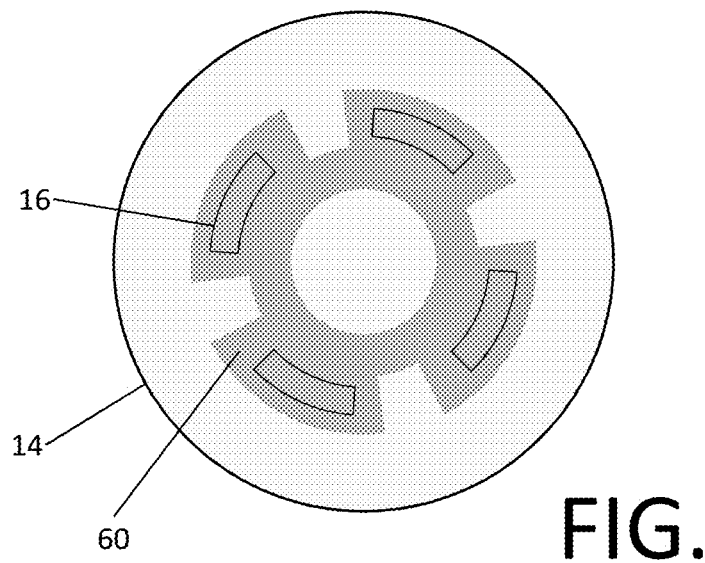
FIG. 15B is a transparent bottom view of a lid with an installed vent closure in a closed position.

FIG. 15B is a transparent bottom view of a lid 14 with an installed vent closure 60 in a closed position. The vents 16 are completely blocked by the vent closure. Although the view is transparent, the handles are not shown for clarity.

Figure 16:
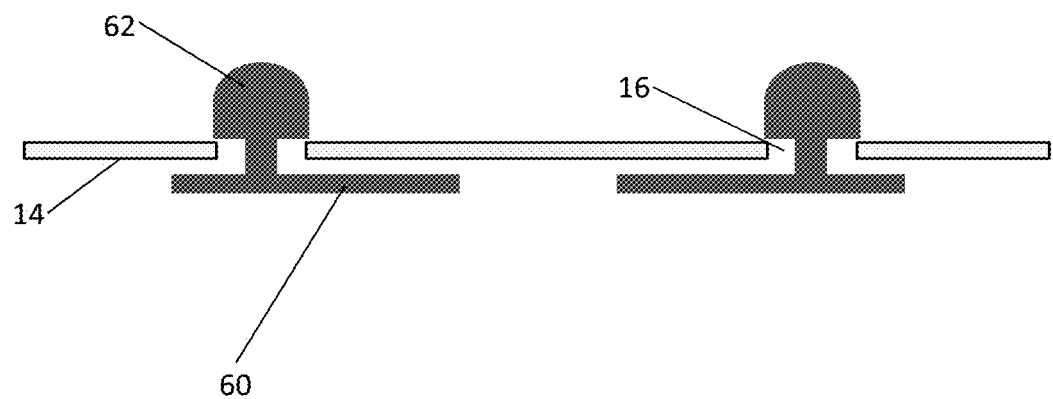
FIG. 16 is a cross-sectional view of the top of a cleaning case with an installed vent closure installed.

FIG. 16 is a cross-sectional view along section a-a' of FIG. 14A, showing the lid 14, vents 16, vent closure 60, and vent closure handle 62. This view shows how the vent handles 62, which snap-fit into the lid 14 from the bottom of the lid, hold the vent closure in place with respect to the lid and provide handles to rotate the vent closure with respect to the lid.

In an alternative embodiment, the plunger stem and vent closure are integral. Thus, the vent closure, which snap-fits into the lid, also holds the plunger to the lid.

It should be understood, of course, that the foregoing relates to exemplary embodiments of the invention and that modifications may be made without departing from the spirit and scope of the invention as set forth in the following claims.

What is claimed is:

1. A cleaning container for holding a retainer or a retainer tray which floats in a liquid under the surface of the liquid, the cleaning container comprising:
    a base adapted to hold the liquid and having a bottom and sides;
    a lid adapted to close against the base and having a top, an underside, and a vent;
    a hinge attaching the lid to the base;
    a vent closure component;
    wherein the base and the lid fit together to seal the container, wherein the vent includes a plurality of curved slots arranged in a circular configuration and the vent closure component is inserted into the curved slots and is operable to rotate to open and close the curved slots;
    a plunger with a disc and a stem, wherein the plunger is immovably affixed to the underside of the lid by the stem, and wherein the disc is slotted to facilitate downward and upward movement of the disc through the liquid and the disc is concave downward so as to prevent the retainer or the retainer tray from slipping off the disc when the inverted container is opened;
    the disc adapted to hold the retainer or the retainer tray below the surface of the liquid by physically contacting the retainer or the retainer tray from above.

2. The container of claim 1, wherein the vent closure component snap-fits into the vent and the vent closure component includes at least one handle for opening and closing the vent.

3. The container of claim 1, wherein the vent closure component and plunger stem are integral.

4. The container of claim 1, further including a strainer basket.

5. The container of claim 1, wherein the stem is a spring-loaded telescoping stem.

6. The container of claim 1, wherein neither the disc nor the container includes spacers for holding the retainer or the retainer tray in place under the liquid.

7. The container of claim 1, wherein the lid and the base snap-fit together.

8. The container of claim 1, wherein the lid includes a recess in the central region on the top of the lid and the vent is peripheral to the recess.

9. The container of claim 1, further comprising a recess, wherein the plurality of curved slots includes four curved slots positioned equidistance from the recess and equidistance from each other, and wherein the base further includes an o-ring, wherein the o-ring provides a seal between the base and the lid when the lid is closed against the base.

10. A cleaning container for holding and cleaning a buoyant dental or orthodontic device, the container comprising:
    a base adapted to hold the liquid and having a bottom and sides;
    a lid adapted to close against the base and having a top, an underside, and a vent;
    a hinge attaching the lid to the base;
    a vent closure component;
    a plunger with a disc and a stem, wherein the plunger is affixed to the underside of the lid by the stem, wherein the disc is adapted to hold the buoyant dental or orthodontic device below the surface of the liquid by physically contacting the buoyant dental or orthodontic device from above;
    wherein the vent includes a plurality of curved slots arranged in a circular configuration, and the vent closure component includes a slot that allows the vent closure component to be slipped around the stem of the plunger, wherein rotation of the vent closure component around the stem of the plunger is operable to open and close the curved slots;
    wherein the disc is concave downward so as to prevent the retainer or retainer tray from slipping off the disc when the cleaning container is inverted and opened; and a sonicator, wherein the sonicator is configured to receive the base and the sonicator is operable to emit ultrasonic waves which agitate particulates on the buoyant dental or orthodontic device.

11. The container of claim 10, wherein the sonicator includes a suction cup to attach the sonicator to a support.

12. A cleaning container for holding a buoyant retainer or a buoyant retainer tray under the surface of a cleaning solution, comprising:
   a base with a bottom and sides, the base adapted to hold the cleaning solution;
   a lid adapted to close against the base and having a top, an underside, and vent holes; and
   a hinge attaching the lid to the base;
   a vent closure component for closing the vent holes, wherein the vent closure component includes handles that fit through the vent holes in the lid to provide external handles for rotating the vent closure component to different positions;
   a plunger with a disc and a stem, wherein the plunger is affixed to the underside of the lid by the stem; and
   wherein the disc is concave downward so as to prevent the retainer or retainer tray from slipping off the disc when the cleaning container is inverted and opened.

13. The container of claim 12, wherein the vent closure component snap-fits into the vent holes.

14. The container of claim 12, wherein the vent closure component is attached to the stem of the plunger.

15. The container of claim 12, further including a strainer basket.

16. The container of claim 12, wherein the stem is a spring-loaded telescoping stem.

17. The container of claim 12, wherein the disc is slotted to facilitate downward and upward movement of the disc through the cleaning solution.

18. The container of claim 12, wherein disc does not include spacers for holding the buoyant retainer or the buoyant retainer tray in place under the cleaning solution.

19. The container of claim 12, wherein when the lid is closed against the base, the disc is positioned approximately one third of the distance from the top of the lid to the bottom of the base to submerge the buoyant retainer or the buoyant retainer tray under the surface of the cleaning solution, and wherein the disc does not contact the container during the closure of the lid.

20. The container of claim 12, wherein the disc is adapted to hold the buoyant retainer or the buoyant retainer tray below the surface of the liquid by physically contacting the buoyant retainer or the buoyant retainer tray from above.

* * * * *